United States Patent [19]
Kanesaka et al.

[11] Patent Number: 5,810,872
[45] Date of Patent: Sep. 22, 1998

[54] FLEXIBLE STENT

[76] Inventors: Nozomu Kanesaka, 36 Cathy Rd.; George A. Tashji, 24 Cathy Rd., both of Hillsdale, N.J. 07642

[21] Appl. No.: 819,566

[22] Filed: Mar. 14, 1997

[51] Int. Cl.⁶ .................................................. A61M 25/00

[52] U.S. Cl. ................... 606/198; 623/1; 623/12

[58] Field of Search ............................... 606/1, 108, 191, 606/194, 195, 198, 200; 623/1, 12

[56] References Cited

U.S. PATENT DOCUMENTS

| | | | |
|---|---|---|---|
| 5,549,663 | 8/1996 | Cottone, Jr. ............................. | 606/195 |
| 5,669,932 | 9/1997 | Fischell et al. .......................... | 606/198 |

FOREIGN PATENT DOCUMENTS

0679372 A2  11/1994  European Pat. Off. .

Primary Examiner—Michael Powell Buiz
Assistant Examiner—William Lewis
Attorney, Agent, or Firm—Kanesaka & Takeuchi

[57] ABSTRACT

An expandable tubular reinforcing member of the invention is used for a body lumen, such as a blood vessel for reinforcement. The reinforcing member is formed of a tortuous section having a plurality of laterally extending elongated members, and a plurality of vertically extending end members situated between two adjacent elongated members for connecting the same. The tortuous section is arranged diagonally to form a cylindrical shape with a first diameter extending in a spiral form. The elongated members generally extend parallel to a central axis of the cylindrical shape. A plurality of joint members is situated between two end members arranged in the cylindrical shape to keep the shape. When a radial force is applied from an inside of the reinforcing member, the elongated members are bent relative to the end members to thereby allow the tubular reinforcing member to have a second diameter larger than the first diameter to thereby hold the body lumen.

15 Claims, 5 Drawing Sheets

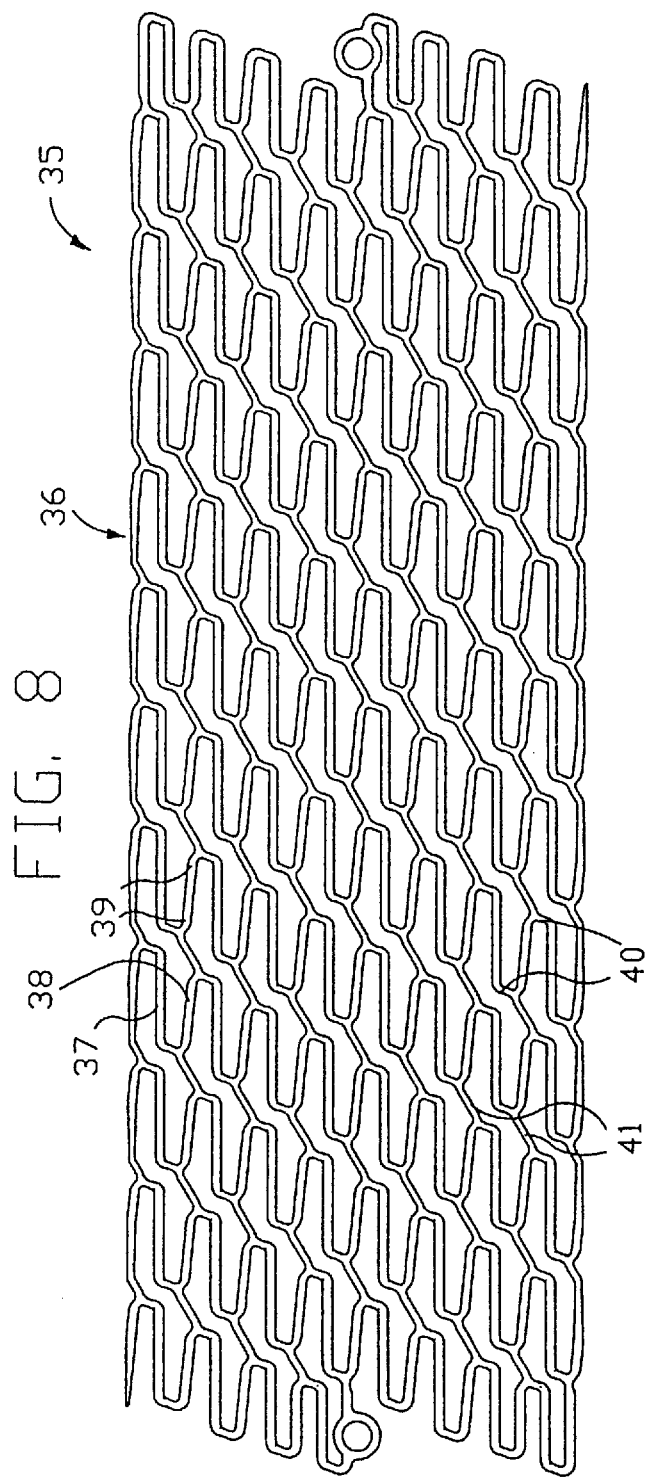

FLEXIBLE STENT

BACKGROUND OF THE INVENTION AND RELATED ART STATEMENT

The invention relates to a flexible stent to be implanted within body lumen, such as an artery, to maintain patency thereof. "Stent" here is defined as a prosthetic member used for reinforcing the blood vessel, and is very useful in the treatment of atherosclerotic stenosis in blood vessels.

When the body lumen is weakened, for example, dissectional artery lining occurs in a body lumen such as a blood vessel, the weak part of the body lumen might collapse to occlude a fluid passageway. To prevent such an occlusion, a stent is implanted within the blood vessel to support the blood vessel from the inside thereof. Namely, a stent is delivered to a desired location in the blood vessel, and expanded in a circumferential direction in the blood vessel to support and maintain the patency of the blood vessel. Using the stent to support the blood vessel can avoid surgical exposing, incising, removing, replacing or bypassing a defective blood vessel required in the conventional vascular surgery.

There have been introduced various types of stents, and they can be typically categorized from viewpoints of methods for expanding the stent, shapes, methods for manufacturing the stent, designs and so on. From a viewpoint of methods for expanding the stent, stents can be categorized as a self-expandable stent which can be expanded by itself, and a balloon expandable stent. In the balloon expandable stent, the stent is mounted on an expandable member, such as a balloon, provided on a distal end of an intravascular catheter, and the catheter is advanced to the desired location in the body lumen to deliver the stent. Then, the balloon on the catheter is inflated to expand the stent into a permanent expanded condition, and the balloon is deflated for removing the catheter from the stent.

From a viewpoint of materials, stents can be categorized into a tubular stent and a wire stent, and from a viewpoint of methods for manufacturing the stent, stents can be categorized as an etched stent and a laser cut stent. Then, from a viewpoint of designs, stents can be categorized into numerous types, but roughly, stents can be categorized into a stent having a zigzag pattern on the surface thereof, and a stent having a diamond pattern on the surface thereof.

Further details of prior art stents can be found in U.S. Pat. No. 5,562,697, U.S. Pat. No. 5,540,713, U.S. Pat. No. 5,575,816, U.S. Pat. No. 5,569,295, U.S. Pat. No. 5,496,365, U.S. Pat. No. 5,344,426, U.S. Pat. No. 5,139,480 and U.S. Pat. No. 5,135,536.

In all types of stents, the stent expands from an initial diameter to a larger diameter so as to be suitable for a particular size of the targeted body cavity. Therefore, the stent must have expandability in the circumferential direction. Also, since the reason why the stent is placed in the body lumen is to support a cavity wall therein to maintain the patency thereof, it is very important that the stent has radial strength as well as support capability.

At the same time, since the stent is generally delivered through torturous path to the desired location in the body lumen, the stent must have flexibility in the axial direction. Namely, the stent must be flexible and is bent easily to thereby facilitate the delivery of the stent in the narrow and meandering body lumen.

In the aforementioned various types, since a wire stent is made by simply bending a wire having flexibility, the wire stent is not only expanded easily, but also shrunk easily. Namely, the wire stent does not have support capability for maintaining the expanded condition in order to keep the body lumen open. On the other hand, a tube type stent has enough support capability to maintain its expanded condition for holding the body lumen open. However, since the tube stent is not flexible in the axial direction, it is difficult to deliver the tube stent in the tortuous lumen to locate the stent in the desirable site.

In the zigzag pattern stent, struts attached in zigzag shape are connected in the circumferential direction to form a tubular shape stent. Therefore, when the stent is expanded, the zigzag shaped struts expand in the circumferential direction, but easily pushed back. Although the zigzag pattern stent has flexibility in the axial direction to facilitate the delivery of the stent in the body lumen, the zigzag pattern stent does not have enough radial strength and support capability to support the body lumen and maintain the patency thereof.

In the stent having a diamond pattern, struts forming diamond shapes are connected in the circumferential direction to form a tubular shape stent. As the diamond pattern stent opens, the diamond shapes expand to give scuffling structure to the stent for excellent radial strength to maintain the patency of the body lumen. The diamond pattern stent, however, has almost no flexibility in the axial direction.

In order to improve axial flexibility in the diamond pattern stent, many attempts have been made by placing flexible curved joints between diamonds, or by removing some joints between diamonds which are connected in the axial direction. These attempts did contributed to improvement for the axial flexibility of the diamond pattern stent in a certain degree, but did not fully improve axial flexibility to be comparable level of the zigzag pattern stent.

Accordingly, an object of the invention is to provide a stent, which has a high degree of flexibility in the axial direction to advance through narrow tortuous passageways.

Another object of the invention is to provide a stent as stated above, which also has strong radial strength and support capability in the circumferential direction.

Further objects and advantages of the invention will be apparent from the following description of the invention.

SUMMARY OF THE INVENTION

To achieve the aforementioned objects of the invention, a stent or an expandable tubular reinforcing member is formed of a tortuous section having a plurality of laterally extending elongated members, and a plurality of vertically extending end members situated between two adjacent elongated members for connecting the same. The tortuous section is arranged diagonally to form a cylindrical shape with a first diameter extending in a spiral form so that the elongated members generally extend parallel to a central axis of the cylindrical shape. A plurality of joint members extends between two end members arranged in the cylindrical shape and situated adjacent to each other. When a radial force is applied from an inside of the reinforcing member, the elongated members are bent relative to the end members to thereby allow the tubular reinforcing member to have a second diameter larger than the first diameter.

In the invention, since the tortuous section is arranged spirally, the stent can be bent easily along the longitudinal direction thereof to thereby facilitate insertion of the stent to a desired portion in the blood vessel.

The tortuous section may be formed of a first tortuous member having a plurality of first lateral members, and a plurality of first vertical members situated between two adjacent first lateral members for connecting the same, the first tortuous member extending continuously from an end to an end; a second tortuous member having a plurality of second lateral members, and a plurality of second vertical members situated between two adjacent second lateral members for connecting the same, the second tortuous member extending continuously from an end to an end; and a plurality of connecting members. Each connecting member is situated between the first and second vertical members to connect the first and second tortuous members together as one unit. The connecting members are arranged diagonally along the periphery of the cylindrical shape in the direction of expansion from the first diameter to the second diameter.

Since the tortuous section is formed of the first and second tortuous members connected by the connecting members, the stent can possess sufficient rigidity as well as longitudinal flexibility.

The elongated members may include long members and short members arranged one after the other. Each short member has inclined ends connected to the end members, and each end of the joint member is connected to both the inclined end and the end member.

BRIEF DESCRIPTION OF THE DRAWINGS

FIG. 8 is a side view of a stent extended in a flat form according to a third embodiment of the invention, which is formed of a plurality of tortuous members.

DETAILED DESCRIPTION OF A PREFERRED EMBODIMENTS

Hereinafter, an embodiment of the present invention is explained with reference to the attached drawings.

Figure 1:
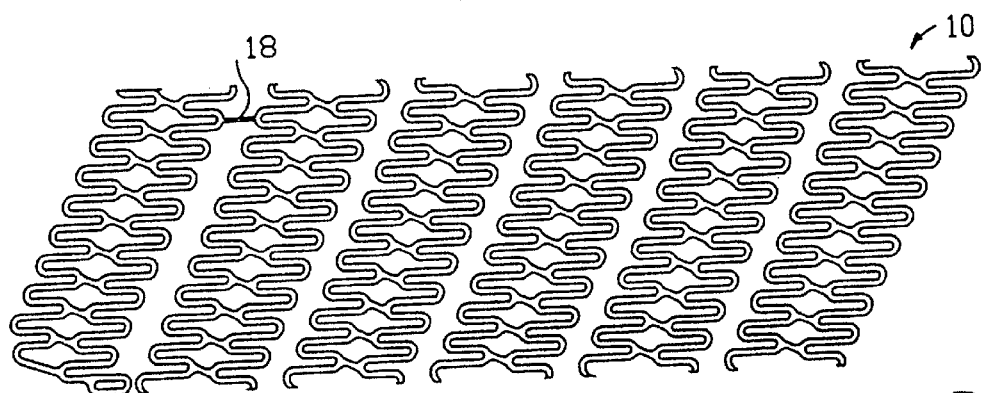
FIG. 1 is a side view of a stent extended in a flat form according to a first embodiment of the invention.
Figure 2:
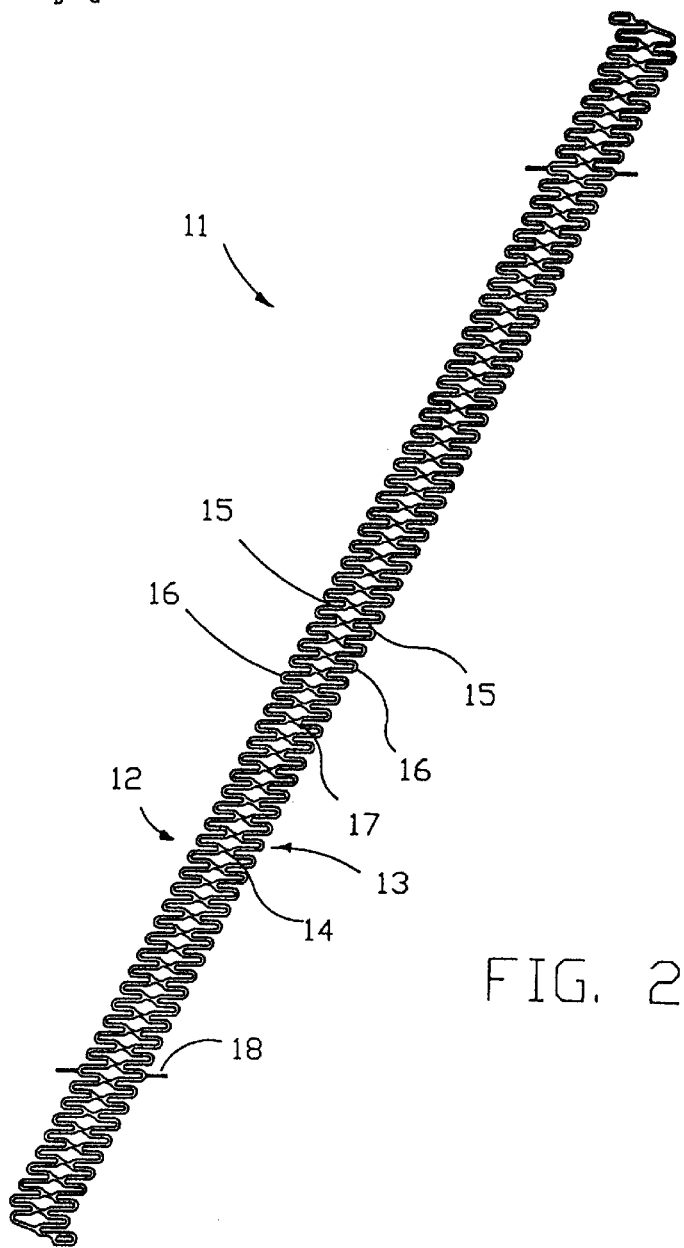
FIG. 2 is a plan view of a strip forming the stent as shown in FIG. 1.
Figure 3:
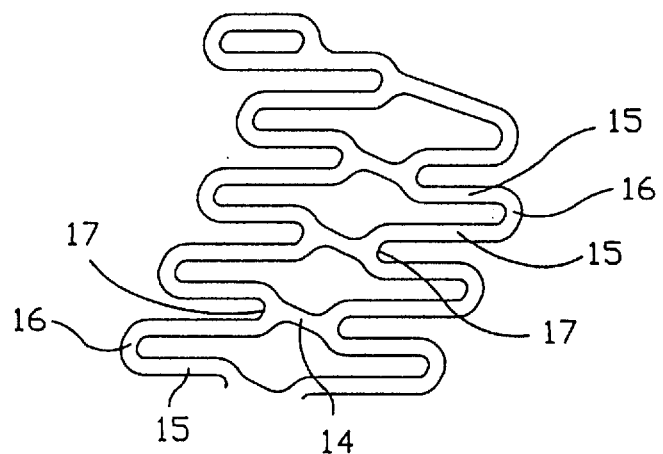
FIG. 3 is an enlarged plan view of a part of the strip shown in FIG. 2.

A stent 10 of a first embodiment of the invention is shown in FIG. 1. The stent 10 is formed of a diagonally arranged strip 11 as shown in FIG. 2, which is wound spirally in a cylindrical shape. The strip 11 includes two tortuous members 12, 13 connected by connecting members or joint struts 14. As shown in FIG. 3, each of the tortuous members 12, 13 is formed of a plurality of parallel members or struts 15 and convex portions 16, 17 for connecting the struts 15. Thus, each tortuous member extends continuously and diagonally in a waving form. The tortuous members 12, 13 are connected by the connecting members 14 at the convex portions 17. The connecting members 14 extend diagonally, so that when the stent 10 is enlarged, the connecting members 14 can be bent easily.

In the embodiment, the strip 11 is formed from a flat metal sheet by etching process or laser cutting. However, it is possible to form the pattern in a metal tube by etching.

Then, in the embodiment of the present invention, the strip 11 is wound spirally in a circular shape, and the wound strip in the circular shape is partly connected by bridge struts 18 to prevent unwinding. The bridge strut 18 should be formed at both ends in the circular shape to keep the shape at the ends, but one or more bridge strut 18 may be formed in the middle portion thereof. No bridge strut 18 may be formed in the middle portion.

In this structure, the stent 10 is formed by simply winding the strip 11 spirally into a circular shape, wherein the portions of the strip 11 situated adjacent to each other are only partly connected together. Therefore, the stent in the circular shape can be easily bent along the axial direction at portions between the adjacent portions. Accordingly, the stent 10 has high flexibility in the axial direction to easily deliver the stent in the tortuous passageway such as body lumens.

In the strip 11 of the invention, the convex portions 17 are connected by the joint strut 14. As compared to a diamond pattern stent in which ends of struts forming one diamond shape are connected to ends of struts forming another diamond shape, the structure of the invention in which the joint strut 14 is connected to the convex portions 17 gives higher stability.

Figure 4:
FIG. 4 is a front view of the stent before it is expanded.
Figure 5:
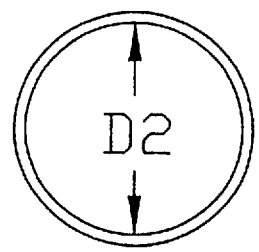
FIG. 5 is a front view of the stent after it is expanded.

When the above constructed stent 10 is implanted in a body lumen, such as an artery, firstly, the stent 10 having an initial diameter $D_1$ (FIG. 4) is delivered into the artery to be located in the desired location. While the stent 10 is delivered in the meandering artery, the stent can be bent easily because of the spiral structure. Then, the stent 10 is expanded to have a second diameter $D_2$ as shown in FIG. 5, which is larger than the initial diameter $D_1$ and is located at the artery wherein the implantation of the stent is necessary. When the stent 10 is expanded to open the passageway in the artery, the parallel struts 15 are inclined at the convex portions 16, 17. Namely, the convex portions 16, 17 are bent, like opening a mouth. The expanded stent 10 has a scuffling structure to have enough stability and strength to prevent the stent 10 from shrinking, so that the artery can be remained open.

Incidentally, when the stent 10 is delivered and expanded, a delivery catheter assembly with an expandable member, such as a balloon, can be used. When the catheter assembly with a balloon is used to deliver the stent 10, the stent 10 is mounted on the balloon, and catheter assembly is pushed into the implantation site. Then, the balloon is inflated for radially applying the force inside the stent 10, and the stent 10 is expanded to have the second diameter $D_2$.

preferably, when the stent 10 is constructed, end portions of the strip are adjusted in lengths, so that the ends of the stent 10 can be straight.

Figure 6:
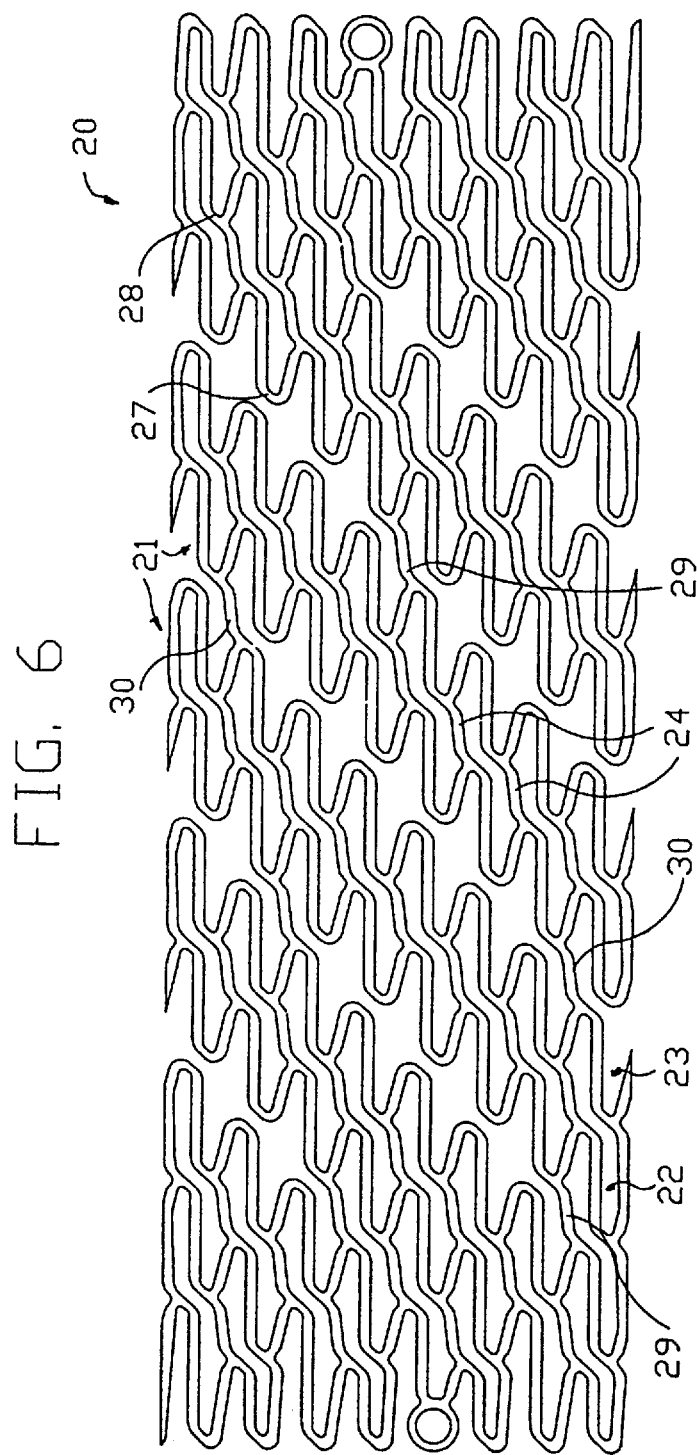
FIG. 6 is a side view of a stent extended in a flat form according to a second embodiment of the invention, wherein two strips are wound to form the cylindrical shape stent.
Figure 7:
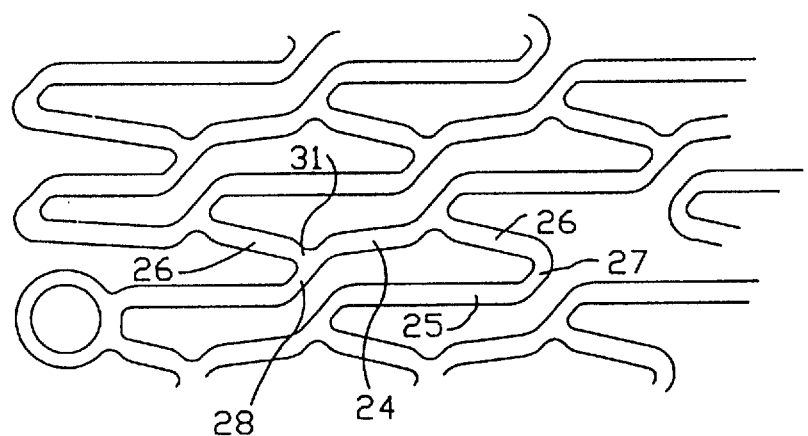
FIG. 7 is an enlarged plan view of a part of the strip forming the stent shown in FIG. 6.

FIGS. 6 and 7 show a second embodiment 20 of a stent of the invention, which is formed by spirally winding two strips 21 situated adjacent to each other. The strip 21 includes two tortuous members 22, 23 connected by connecting members or joint struts 24. As shown in FIG. 7, each of the tortuous members 22, 23 is formed of a plurality of struts 25, 26 and convex or connecting portions 27, 28 for connecting the struts 25, 26. The struts 25 extend substantially parallel to the central axis of the stent 20, but the struts 26 slightly incline in the expanding direction. The struts 25, 26 may slightly incline in a vertical direction relative to the central axis. Each tortuous member extends continuously and diagonally in a waving form. The tortuous members 22, 23 are connected by the diagonal connecting members 24 at the convex portions 28.

In the embodiment 20, two strips 21 are jointed by joining members 29 and are wound spirally in a circular shape, and the wound strips in the circular shape are partly connected by bridge struts 30 to prevent unwinding. The jointed members 29 and the bridge struts 30 may be straight or curved.

As shown in an enlarged view of a part of the strips 22 of FIG. 7, each portion 31 at which the strut 26 is connected to the convex portion 28 has a size smaller than that of a middle portion thereof. Also, end portions of the joint strut 24 have a size smaller than that of the middle portion thereof. Therefore, when the stent 20 is opened, the struts 24, 26 can be bent easily. In the stent 20, when it is expanded, the connecting portions 27, 28 do not change the positions, and the struts 24, 25, 26 are bent relative to the connecting portions 27, 28. The stent 20 operates as in the stent 10.

FIG. 8 shows a third embodiment 35 of the stent of the invention. The stent 35 is formed of a plurality of tortuous members 36 spirally arranged in a cylindrical form. The tortuous member 36 includes long struts 37, and short struts 38 with inclined portions 39 at both ends. Connecting portions 40 connect the short and long struts 37, 38 to form the tortuous member 36. The tortuous members 36 situated adjacent to each other are connected by joint struts 41. The stent 35 can be used as in the first and second embodiments.

When a stent is expanded, in general, force is applied to the ends of the stent. In order to open the stent 35 easily and equally throughout the entire length thereof, the size of the end portions 39 of the strut 38 is made small. Alternatively, end portions of the strut 41 can be set to have a smaller size than those of struts and the middle portion of the strut. Accordingly, when the stent is expanded, the strut 41 can be bent at the ends with the smaller size so as to avoid warping.

In the present invention, since the tortuous member is arranged spirally, the stent can be bent in the longitudinal direction relatively easily when the stent is placed in a patient body. Also, the stent of the invention can be opened easily and holds the pressure applied thereto after it is expanded.

While the invention has been explained with reference to the specific embodiments of the invention, the explanation is illustrative and the invention is limited only by the appended claims.

What is claimed is:

1. An expandable tubular reinforcing member used for a body lumen comprising,
    a tortuous section having a plurality of laterally extending elongated members formed of one kind of long members and one kind of short members arranged one after the other, and a plurality of vertically extending end members situated between two adjacent elongated members for connecting the same, said tortuous section being arranged diagonally to form a cylindrical shape with a first diameter and extending in a spiral form so that the elongated members generally extend along a central axis of the cylindrical shape, and
    a plurality of joint members extending between two end members arranged in the cylindrical shape and situated adjacent to each other so that when a radial force is applied from an inside of the reinforcing member, the elongated members are bent relative to the end members to thereby allow the tubular reinforcing member to have a second diameter larger than the first diameter.

2. An expandable tubular reinforcing member used for a body lumen comprising,
    a tortuous section having a plurality of laterally extending elongated members, and a plurality of vertically extending end members situated between two adjacent elongated members for connecting the same, said tortuous section being arranged diagonally to form a cylindrical shape with a first diameter extending in a spiral form so that the elongated members generally extend along a central axis of the cylindrical shape, and
    a plurality of joint members extending between two end members arranged in the cylindrical shape and situated adjacent to each other so that when a radial force is applied from an inside of the reinforcing member, the elongated members are bent relative to the end members to thereby allow the tubular reinforcing member to have a second diameter larger than the first diameter, wherein said tortuous section includes:
        a first tortuous member having a plurality of first lateral members, and a plurality of first vertical members situated between two adjacent first lateral members for connecting the same, said first tortuous member extending continuously from an end to an end,
        a second tortuous member having a plurality of second lateral members, and a plurality of second vertical members situated between two adjacent second lateral members for connecting the same, said second tortuous member extending continuously from an end to an end, said first and second lateral members constituting the elongated members and said first and second vertical members constituting the end members, and
        a plurality of connecting members, each being situated between the first and second vertical members to connect the first and second tortuous members together as one unit, said connecting members being arranged diagonally along the periphery of the cylindrical shape in the direction of expansion from the first diameter to the second diameter.

3. An expandable tubular reinforcing member according to claim 2, wherein said first lateral members are arranged parallel to each other; each of the first vertical members is curved to protrude outwardly relative to the first lateral members; the second lateral members are arranged parallel to each other; and each of the second vertical members is curved to protrude outwardly relative to the second lateral members.

4. An expandable tubular reinforcing member according to claim 3, wherein said joint members are formed to connect some of the first and second vertical members.

5. An expandable tubular reinforcing member according to claim 2, wherein said first lateral members include long members and short members arranged one after the other, said short members inclining slightly toward a bending direction thereof; and said second lateral members include long members and short members arranged one after the other, said short members inclining slightly toward a bending direction thereof.

6. An expandable tubular reinforcing member according to claim 5, wherein said long and short members of the first and second lateral members have sectional dimensions smaller at end portions than at middle portions to facilitate bending of the long and short members.

7. An expandable tubular reinforcing member according to claim 6, wherein said joint members extend diagonally along the periphery of the cylindrical shape in the direction of expansion from the first diameter to the second diameter.

8. An expandable tubular reinforcing member according to claim 2, wherein a plurality of said unit, each being formed of the first and second tortuous members and the connecting members, is arranged side by side and wound in the spiral form.

9. An expandable tubular reinforcing member according to claim 1, wherein each short member has inclined ends connected to the end member, each end of said joint member being connected to both of the inclined end and the end member.

10. An expandable tubular reinforcing member according to claim 1, wherein one of two kinds of the long and short members extends parallel to the central axis of the cylindrical shape, and the other of the two kinds of the long and short members inclines relative to said one kind in a direction of expansion from the first diameter to the second diameter.

11. An expandable tubular reinforcing member according to claim 10, wherein said long members extend parallel to the central axis, and the short members incline relative to the long members.

12. An expandable tubular reinforcing member used for a body lumen comprising, a tortuous section including a plurality of laterally extending elongated members formed of first and second members arranged one after the other, and a plurality of vertically extending end members situated between two adjacent elongated members for connecting the same, said tortuous section extending in a spiral form to form a cylindrical shape with a first diameter so that locations of the end members gradually change from one side to the other side of the cylindrical shape along a central axis thereof, said first members extending substantially parallel to the central axis of the cylindrical shape, and a plurality of joint members extending between two end members arranged in the cylindrical shape and situated adjacent to each other so that when a radial force is applied from an inside of the reinforcing member, the elongated members are bent relative to the end members to thereby allow the tubular reinforcing member to have a second diameter larger than the first diameter.

13. An expandable tubular reinforcing member according to claim 12, wherein said first and second members have sectional dimensions smaller at end portions than at middle portions to facilitate bending of the long and short members.

14. An expandable tubular reinforcing member according to claim 13, wherein said second members incline relative to the first members in a direction of expansion from the first diameter to the second diameter.

15. An expandable tubular reinforcing member according to claim 12, wherein the end members, which constitute parts of the tortuous section and face each other when the tortuous section is arranged in the cylindrical shape, are all connected together by the joint members extending spirally.

* * * * *